US005554177A

United States Patent [19]

Kieval et al.

[11] Patent Number: 5,554,177
[45] Date of Patent: Sep. 10, 1996

[54] METHOD AND APPARATUS TO OPTIMIZE PACING BASED ON INTENSITY OF ACOUSTIC SIGNAL

[75] Inventors: Robert S. Kieval, Golden Valley; Orhan Soykan, New Brighton, both of Minn.

[73] Assignee: Medtronic, Inc., Minneapolis, Minn.

[21] Appl. No.: 411,241

[22] Filed: Mar. 27, 1995

[51] Int. Cl.$^6$ .................................................. A61N 1/39
[52] U.S. Cl. ............................................. 607/17; 607/18
[58] Field of Search ................................. 607/9, 17, 18

[56] References Cited

U.S. PATENT DOCUMENTS

| | | | |
|---|---|---|---|
| 4,257,423 | 3/1981 | McDonald | 607/30 |
| 4,374,382 | 2/1983 | Markowitz | 607/27 |
| 4,428,378 | 1/1984 | Anderson | 607/19 |
| 4,556,063 | 12/1985 | Thompson | 607/32 |
| 4,600,017 | 7/1986 | Schroeppel | 607/122 |
| 4,708,143 | 11/1987 | Schroeppel | 607/17 |
| 4,763,646 | 8/1988 | Lekholm | 607/14 |
| 5,012,815 | 5/1991 | Bennett, Jr. et al. | 128/715 |
| 5,024,222 | 6/1991 | Thacker | 607/22 |
| 5,025,809 | 6/1991 | Johnson et al. | 128/715 |
| 5,052,388 | 10/1991 | Sivula | 607/22 |
| 5,127,404 | 7/1992 | Wyborny | 607/32 |
| 5,156,157 | 10/1992 | Valenta | 128/662.06 |
| 5,183,040 | 2/1993 | Nappholz | 607/4 |
| 5,301,679 | 4/1994 | Taylor | 128/773 |
| 5,334,220 | 8/1994 | Sholder | 607/9 |
| 5,334,222 | 8/1994 | Salo et al. | 607/17 |
| 5,340,361 | 8/1994 | Sholder | 607/9 |
| 5,411,531 | 5/1995 | Hill et al. | 607/9 |

OTHER PUBLICATIONS

Ishikawa et al., "Critical PQ Interval for the Appearance of Diastolic Mitral Regurgitation and Optimal PQ Interval in Patients Implanted with DDD Pacemakers," PACE, vol. 17, Nov. 1994, Part II, pp. 1989–1994.

Fananapazir, et al., "Impact of Dual–Chamber Permanent Pacing in Patients with Obstructive Hypertrophic Cardiomyopathy with Symptoms Refraactory to Verapamil and β–Adrenergic Blocker Therapy", *Circulation*, 85(6):2149–61, Jun. 92.

Jeanrenaud et al., "Effects of Dual–Chamber Pacing in Hypertrophic Obstructive Cardiomyopathy", *The Lancet*, 1992; May 30, 1992, vol. 339; 1318–23.

Kappenberger, J., "The Optimal Patient for Pacemaker–Treatment of Hypertrophic Obstructive Cardiomyopathy (HOCM)," *Pace*, vol. 16, May 1993, Part II, p–1120.

McAreavey, et al., "Altered Cardiac Hemodynamic and Electrical State in Normal Sinus Rhythm After Chronic Dual–Chamber Pacing for Relief of Left Ventricular Outflow Obstruction in Hypertrophic Cardiomyopathy", *American Journal of Cardiology*, 70(6):651–6 Sep. 1, 192, pp. 651–656.

McDonald, et al., "Permanent Pacing as Treatment for Hypertrophic Cardiomyopathy", *American Journal of Cardiology*, 68(1): 108–110 Jul. 1991, pp. 108–110.

Seidelin et al., "Effects of Dual–Chamber pacing in Hypertrophic Cardiomyopathy Without Obstruction", *The Lancet*, 340(8815):369–70, Aug. 8, 1992.

Gras, "How to Optimize Pacing Therapy in Patients with Hypertrophic Obstructive Cardiomyopathy: The Importance of AV Delay Programming". *Pace*, vol. 16, May 1993, Part II, p–1121.

(List continued on next page.)

Primary Examiner—Carl H. Kamm
Assistant Examiner—Carl H. Layno
Attorney, Agent, or Firm—Harold R. Patton; Michael B. Atlass

[57] ABSTRACT

An acoustic sensor is located in association with a patient's heart to detect abnormal heart sounds and a processor isolates abnormal heart sounds therefrom. The characteristics of these heart sounds are monitored while adjustments are made to the timing of pacing pulses to achieve a better heart function through pacing therapy. Particular adaption to cardiomyopathy is shown.

17 Claims, 6 Drawing Sheets

OTHER PUBLICATIONS

Brecker et al., "Effects of Dual–Chamber Pacing with Short Atrioventricular Delay in Dilated Cardiomyopathy", *The Lancet,* vol. 340:Nov. 28, 1992 p. 1308.

Ishikawa, et al., "Critical PQ Interval for the Appearance of Diastolic Mitral Regurgitation and Optimal PQ Interval in Patients Implanted with DDD Pacemakers", *PACE,* vol. 17, Nov. 1994, Part II, p. 1989.

"The Doctor's World", New York Times, Tuesday, Mar. 2, 1993, p. B6.

"Dual Chamber Pacing Therapy for Hypertrophic Obstructive Cardiomyopathy", Rob Kieval VMD, PhD, *Medtronic Science & Technology Journal,* Nov. 1993, p. 2.

"Outcome of Mitral Regurigitation in Obstructive Hypertrophic Cardiomyopathy Treated by DDD Pacing", *Circulation,* vol. 90, No. 4, Part 2, Oct 1994, p. I–443.

"Unusual Use of Pacemaker to Help Aspin's Heart Raises Possibility of New Market for Medtronic", Steve Gross.

"Prognosis Good as Aspin Gets Pacemaker", Associated Press, Washington D.C.

"Aspin Undergoes Surgery For Pacemaker Implant", John Lancaster, *Washington Post.*

METHOD AND APPARATUS TO OPTIMIZE PACING BASED ON INTENSITY OF ACOUSTIC SIGNAL

BACKGROUND OF THE INVENTION

This invention relates primarily to sounds generated by the beating heart in the audible range and their use for adaptive pacing and has particular application to optimized pacing for congestive heart failure including but not limited to conditions known as hypertrophic and dilated cardiomyopathy as well as other conditions associated with turbulent or other aberrant blood flow conditions in the heart. Its teaching may be applied to hemodynamic control generally.

Over the centuries heart sounds have been used to monitor heart function by practitioners of medicine. Even today when one visits a doctor's office, almost invariably monitoring one's heart sounds through a stethoscope is conducted by examining physicians.

Nevertheless, these direct sound signals generated by the heart have not been used previously to optimize the timing of pacing pulses delivered to a paced heart. Because the conditions of hypertrophic and dilated cardiomyopathy may be associated with acoustical range noises made by the heart related to mitral valvular regurgitation it can be demonstrated that this indication provided by these sounds can be put to use. The direct employment of this diagnostic parameter to the pacing of the heart has not, however, been previously employed nor has any apparatus or system been developed to take advantage of this naturally occurring indicator.

In order to take advantage of this useful feature, the invention here adjusts the pacemaker AV delay (which may also be called "AV interval" or "AV escape interval") by reference to the sound signals generated by the heart. The literature supports the concept of adjustment of the AV delay to optimize pacing particularly in Hypertrophic Obstructive Cardiomyopathy (HOCM) patients. This invention bases the AV interval timing or adjustment on sound and shows how it can be applied to HOCM and other congestive heart patients.

For a discussion on how to adjust the electrocardiographic PQ interval by setting the AV delay with a DDD pacemaker, see "Critical PQ Interval for the Appearance of Diastolic Mitral Regurgitation and Optimal PQ Interval in Patients Implanted with DDD Pacemakers" by Ishikawa et al., PACE, Vol. 17, November, 1994, Part II.

Two United States patents also illustrate adaptively changing the AV interval (or "PV" interval in one case) both to avoid fusion with the natural ventricular depolarization of a patient's heart and to assist patients suffering from cardiomyopathy to improve cardiac output. See Sholder, U.S. Pat. Nos. 5,340,361 and 5,334,220.

The value of dual chamber cardiac pacing in treatment of patients suffering from HOCM has been recognized and the benefits of this therapy are discussed in the articles "Permanent Pacing as Treatment for Hypertrophic Cardiomyopathy" by Kenneth M. McDonald et al., published in the *American Journal of Cardiology*, Vol. 68, Jul. 1, 1991, pp. 108–110, "Impact of Dual Chamber Permanent Pacing in Patients with Obstructive Hypertrophic Cardiomyopathy with Symptoms Refractory to Verapamil and β-Adrenergic Blocker Therapy" by Fananapazir et al., published in *Circulation*, Vol. 8, No. 6, June, 1992, pp. 2149–2161, "Effects of Dual-Chamber pacing in Hypertrophic Obstructive Cardiomyopathy", by Jeanrenaud, et al., published in *The Lancet*, Vol. 33, May 30, 1992, pp. 1318–1323, "Altered Cardiac Hemodynamic and Electrical State in Normal Sinus Rhythm After Chronic Dual-Chamber Pacing for Relief of Left Ventricular Outflow Obstruction in Hypertrophic Cardiomyopathy", by McAreavey et al., published in *American Journal of Cardiology*, 1992, Vol. 70, pp. 651–656, and "Effects of Dual-Chamber Pacing in Hypertrophic Cardiomyopathy Without Obstruction", by Seidelin et al., published in *The Lancet*, 1992, pp. 340–369. In these papers, the value of DDD pacing employing a shortened A-V escape interval is discussed. In particular, the use of an A-V escape interval which is shorter than the patient's intrinsic A-V conduction is specifically recommended, with favorable results being reported so long as the duration of the pacemaker's A-V escape interval is not so short that hemodynamic performance is compromised. Various approaches to selecting the optimal A-V escape interval are discussed in the literature, but none are based on heart sounds. In the cited studies, the favored signal to use for adjustment of the AV delay is a processed Doppler signal, which in the current state of the art cannot easily be done with an unassisted implantable device. Physicians have in the past used Doppler measurements of the subaortic pressure gradient to adjust the AV interval. Doppler measurements require significant processing time and power to yield useful data signals and additional sensing and output hardware. If direct sound volume signals are used the device can be much simpler. See, "Effects of Dual Chamber Pacing with Short Atrioventricular Delay in Dialated Cardiomyopathy", Brecker et al., *The Lancet*, Vol. 340, Nov. 28, 1992, pp. 1308–12 for an example of current usage of phonocardiogram versus Doppler, (esp. FIG. 1).

In making AV delay adjustments, pre-excitation of the ventricular apex and septum by the ventricular pacing pulse prior to excitation due to natural conduction between the atrium and ventricle is generally preferred. The abstract "How to Optimize Pacing Therapy in Patients with Hypertrophic Obstructive Cardiomyopathy: The Importance of AV Delay Programming" by Gras, et al., published in *PACE*, May, 1993, Vol. 16, Part II, page 1121 suggests that the longest A-V escape interval which provides complete ventricular capture should be selected. The above-cited article by Fananapazir suggests that the A-V escape interval which allows for maximal pre-excitation of the ventricle by the pacing pulse can be selected by employing the A-V escape interval that produces the widest paced QRS complex duration. The above-cited McDonald article suggests that the A-V escape interval should be set at the longest duration that maintains ventricular capture at maximum exercise levels.

In the abstract "The Optimal Patient for Pacemaker Treatment of Hypertrophic Obstructive Cardiomyopathy (HOCM)" by Jeanrenaud et al, published in *PACE*, May, 1993, Vol. 16, Part II, page 1120, it is suggested that in the case of patients who would require an excessively short A-V escape interval in order to accomplish pre-excitation, intrinsic A-V conduction time could be prolonged by means of drugs or ablation techniques.

We believe these references establish that there is an optimal range of AV delay to produce maximum hemodynamic benefits through pacing. This optimal AV delay is also expected to be associated with a minimum degree of mitral valvular regurgitation. Other studies have established that the curve of pulmonic artery pressure (a measure of hemodynamic function) versus AV delay has a theoretical local minimum below the range of optimal AV delay. Accordingly, in adjusting the AV delay, one must be careful not to overlengthen or overshorten it if there are to be benefits to the therapy.

BRIEF DESCRIPTION OF THE DRAWINGS

FIG. 6 is a diagram of a heart showing placement of electrodes.

SUMMARY OF THE INVENTION

Figure 1:
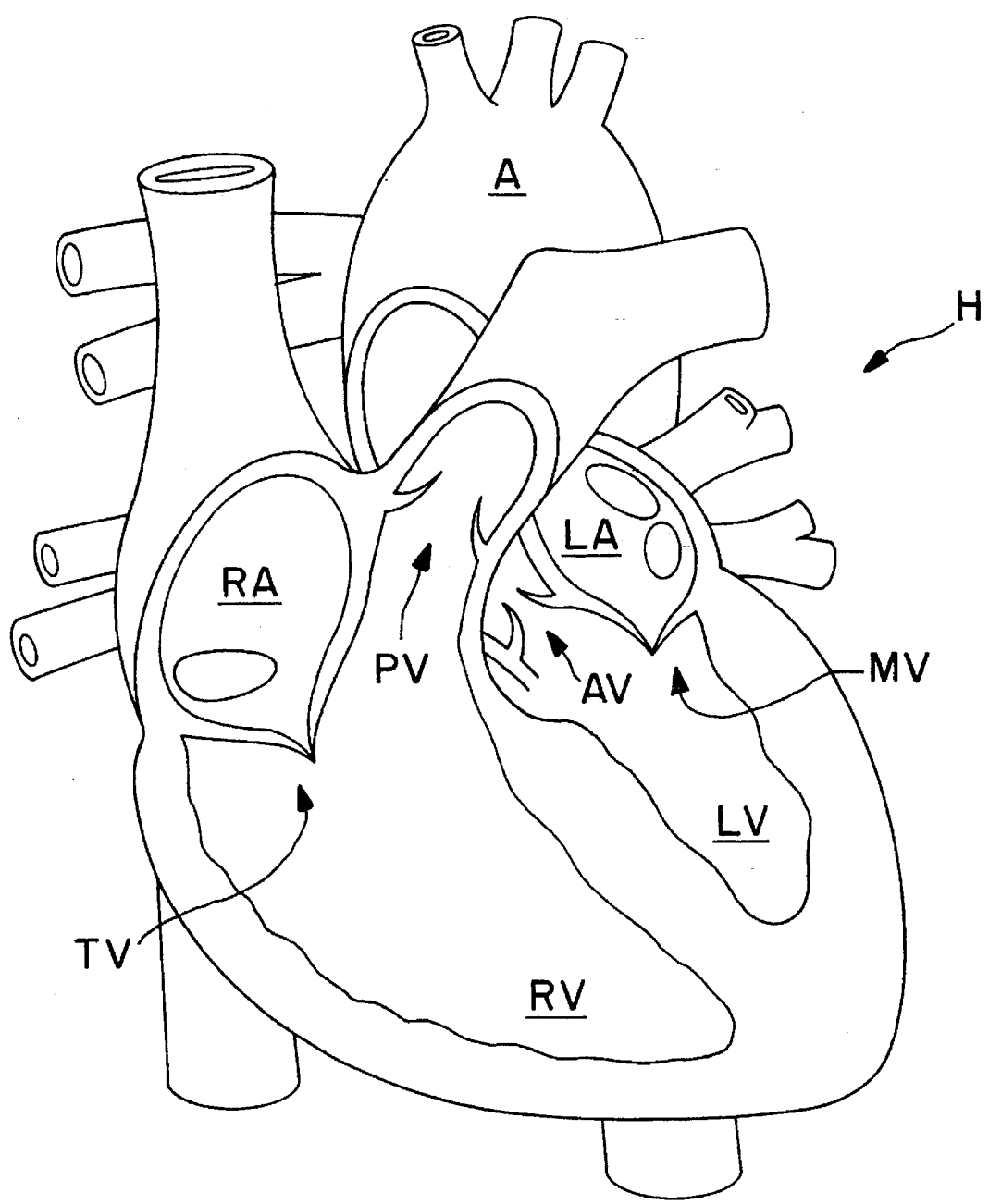
FIGS. 1, 2 and 6 are cutaway illustrations of the human heart illustrating various conditions for the purposes of explaining the invention.

A method and apparatus are described which adjust a cardiac pacemaker by automatically responding to acoustic feedback generated by the heart sound which accompanies (in time) an abnormal heart sound. The preferred sound to adjust for is mitral regurgitation (also called "MR"). This requires first the determination of the temporal location between the first ($S_1$) and the second ($S_2$) heart valve sounds from the signal produced by an acoustic sensor adaptively associated with the heart. The volume of this signal (or some measure of its intensity) is used to determine the appropriate AV delay for pacing pulse timing by adjusting the AV delay until the intensity of the abnormal sound is at its lowest volume. At the same time it must be recognized that the optimum AV delay is something greater than zero which will also cause the MR sound to disappear and to avoid an expected local minimum below 50 ms from the atrial pulse initiation. The preferred range is approximately 60 to 150 microseconds and the method used to adjust the delay will find the preferred AV delay somewhere close to within that range or recognize that it may be trapped in a local minimum.

The invention uses an acoustic sensor located (preferably) in the patient's body disposed to pick up the abnormal sound signature (preferably of MR) when it occurs during the cardiac cycle. A processor for determining the sound's signature and its volume from the output of the sensor and initiating an iterative process to reduce the abnormal heart sound signal to its minimum intensity by changing the timing of the AV delay through pacing must also be included.

These adjustments to AV delay can occur in several ways. In a clinical setting, an external programmer may be used to make the adjustments on a periodic or initial basis upon the insertion of the pacemaker into the patient. If this is the mode, the programmer may use an externally located sound sensor. Alternatively, and preferably, the cardiac pacemaker may have an associated acoustic sensor which delivers sounds signals to it automatically and allows it to periodically adjust itself in response to the detected abnormal heart sound signals. As is well known in the pacemaker art programmers which are used to communicate with pacemakers can do so through telemetry circuits, either at implant time or during follow up. Also known are pacing system analyzers which can communicate through wire or telemetrically with the pacemaker, but these are sues almost exclusively during implant or replacement procedures. In either case, simple modification of the AV delay interval or other mechanism in the pacemaker that determines AV interval through one of these communication systems would allow for use of this invention in the clinical setting at the direct control of a human operator.

Additional applications of this invention may be made to other than MR heart sounds for adjusting pacing.

In the preferred form the adjustments are made according to the equation:

$$AV\ delay_{N+1} = AV\ delay_N(1 + a(MRSA_N - MRSA_{N-1}))$$

to adjust the AV delay for each new heart cycle "$_{N+1}$", wherein each $_N$ indicates a heart beat cycle, $_{N-1}$ indicates a heart beat cycle previous to $_N$, $MRSA_N$ is the MR sound amplitude for heart cycle $_N$ and a is the gain for the system response.

Also, this equation can be generalized to:

$$delay_{N+1} = delay_N(1 + a(SA_N - SA_{N-1}))$$

to adjust the pulse timing delay for each new heart cycle "$_{N+1}$", wherein each $_N$ indicates a heart beat cycle, $_{N-1}$ indicates a heart beat cycle previous to $_N$, $SA_N$ is the one particular heart sound amplitude for heart cycle $_N$ and a is the gain for the system response.

DETAILED DESCRIPTION OF A PREFERRED EMBODIMENT OF THE INVENTION

While it is true that listening to heart sounds has been a practice of physicians throughout the centuries, it is useful to explain the fundamentals of the process.

Referring first to FIG. 1, a human heart is illustrated having a right ventricle RV, a left ventricle LV, an aorta A, pulmonary artery PA, right atrium RA and left atrium LA illustrated. The valves of the heart include the mitral valve MV and the tricuspid valve TV, also known as the "atrioventricular valves"; and the pulmonic valve PV and the aortic valve AV also known as the "semi-lunar valves".

With reference to FIG. 1, the heart sound generated ($S_1$) is thought to occur because of the closing of the atrioventricular valves as well as associated deceleration and turbulence of the blood flow. This sound is colloquially referred to as the "Lub" part of the Lub-Dub rhythm of the heart sounds.

Figure 2:
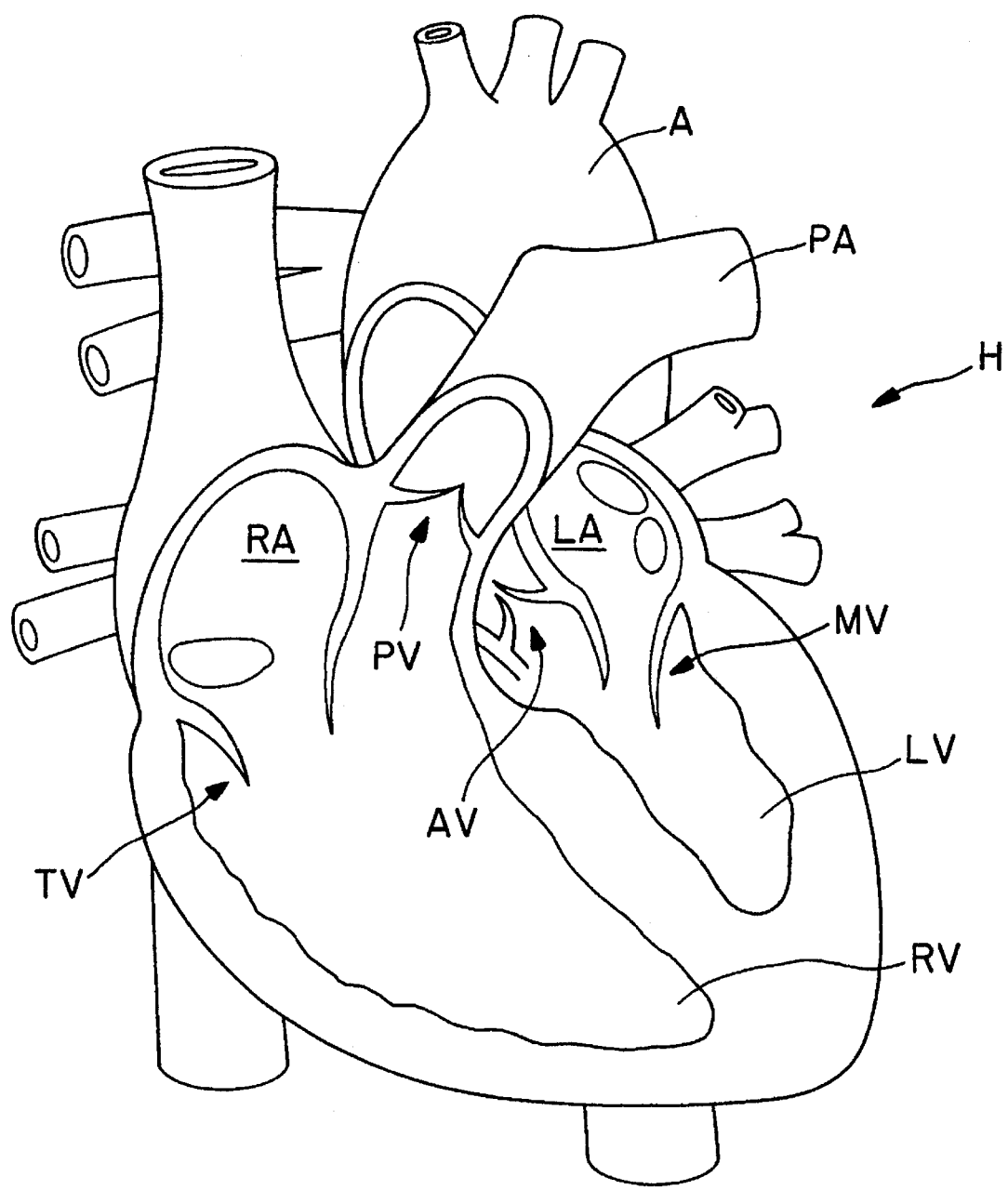

In FIG. 2, the other position of the valves is shown with the pulmonic valve and aortic valves closed and the mitral and tricuspid valves beginning to open. This condition occurs coincident with the second major heart sound (Dub) and is thought to be caused by the closing and reverse pressure against the semilunar valves as the heart's ventricles relax.

Figure 3:
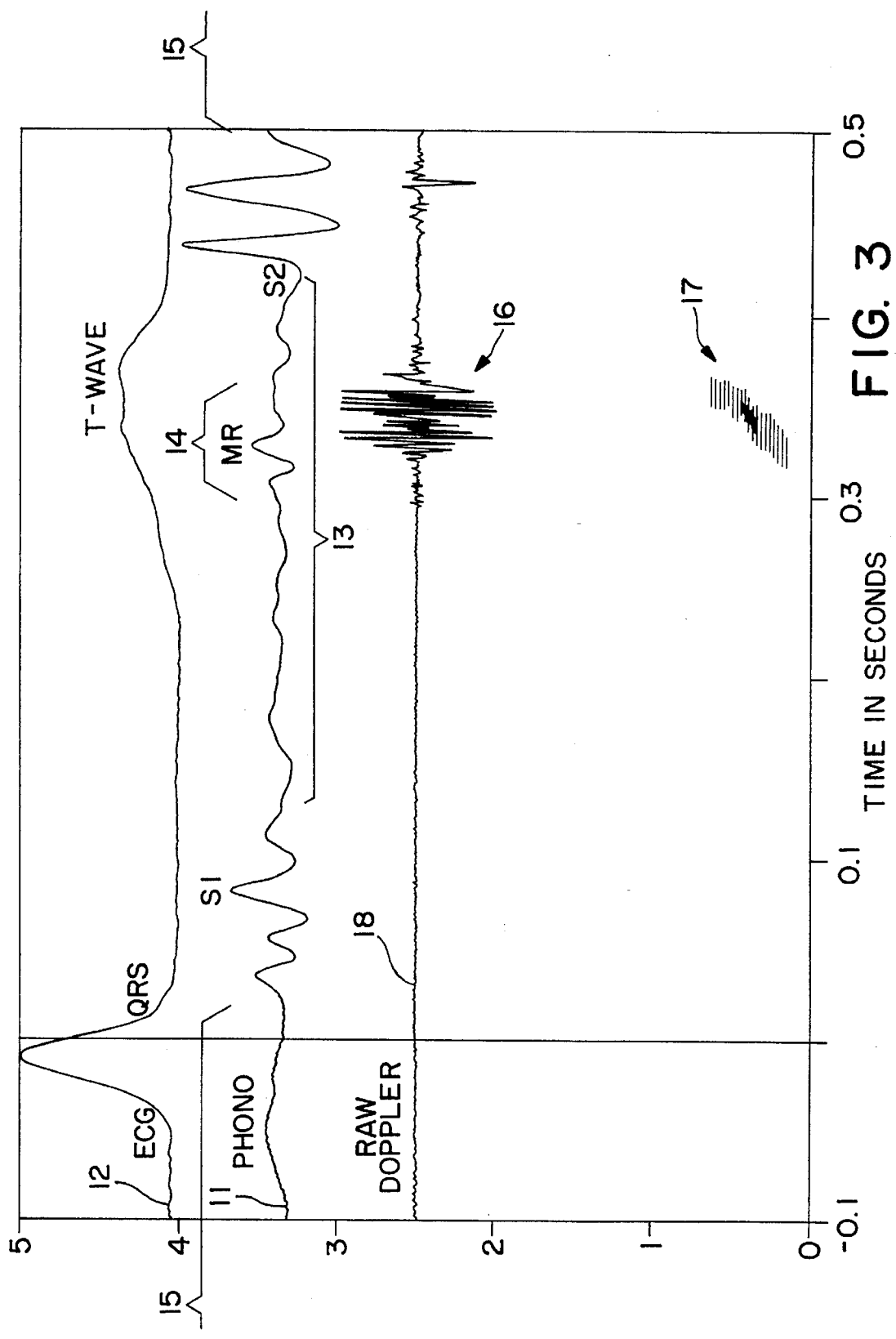
FIG. 3 is a graph over time of electrical and auditory signals generated by the heart.

The audio record produced by these two heart sounds is illustrated in FIG. 3 by line 11, that is, sound $S_1$ corresponds generally to the "Lub" sound of the configuration of the heart illustrated in FIG. 1, and the $S_2$ feature of curve 11 corresponds to the FIG. 2 or "Dub" sound of the heart. Sounds in the audible range which occur between $S_1$ and $S_2$ area 13 are considered by diagnostic physicians to be systolic murmurs (with one indicated at 14) and at times after $S_2$ but preceding $S_1$ diastolic murmurs in area 15.

Also illustrated in FIG. 3 are temporally coincident signals generated by an electrocardiogram (line 12) and Doppler 16 and processed Doppler signal 17 waveforms. The implanted pulse generator for dual chamber pacing usually has the electrocardiogram available since it is sensing for depolarizations, but the Doppler signals have only been available with external equipment used to generate and decode Doppler echoes.

In order to produce the clearest signal from output similar to that illustrated in FIG. 3, line 11, the placement and location of acoustic detectors or microphones can be crucial. While substantial experimentation continues in this area, two appropriate and presently preferred places for implantable acoustic sensors have emerged including locations 21 and 22 illustrated with reference to the body B and the heart H of FIG. 4. The location illustrated by the area identified by features 21 and 23 suggests the possibility that the acoustic detector be located within the "can" or container for the pulse generator associated with the heart H. Location 22 is up against the sternum bone in the center of the chest which provides for a large solid piece of bone against which the acoustic sensor may rest.

It is known that achieving acoustic output with a high signal to noise ratio is made more difficult by ambient noise in the environment and by movement of the body. Accordingly, the application of this invention should be directed to times and locations at which the body is at rest and quiet. Numerous accompanying devices and techniques may be employed including activity sensors such as implanted accelerometers, respiration detectors, posture sensors, an internal clock and so forth where this invention is used to automatically adjust pacing. This availability of other sensors is common in rate responsive pacing. One method and apparatus would be to have the patient in a quiet room during which time an acoustic sensor is located by a physician at a given location on the patient's body each time the adjustment is made. The use of the invention in this form, of course, precludes automatic adjustment by the pacemaker itself without intervention by the patient or his physician. Depending on the type of abnormal sound being employed with this invention, various characteristics of that sound may be employed. For example, the amplitude or volume of the MR sound is presently most preferred, but the duration of the signal may also be used as the signal characteristic that the algorithm seeks to lower. Of course a product of these two signal measures could also be used. The reader will recognize that the electronics apparatus for finding and measuring the sound signal will vary in accord with the characteristic chosen.

Figure 4:
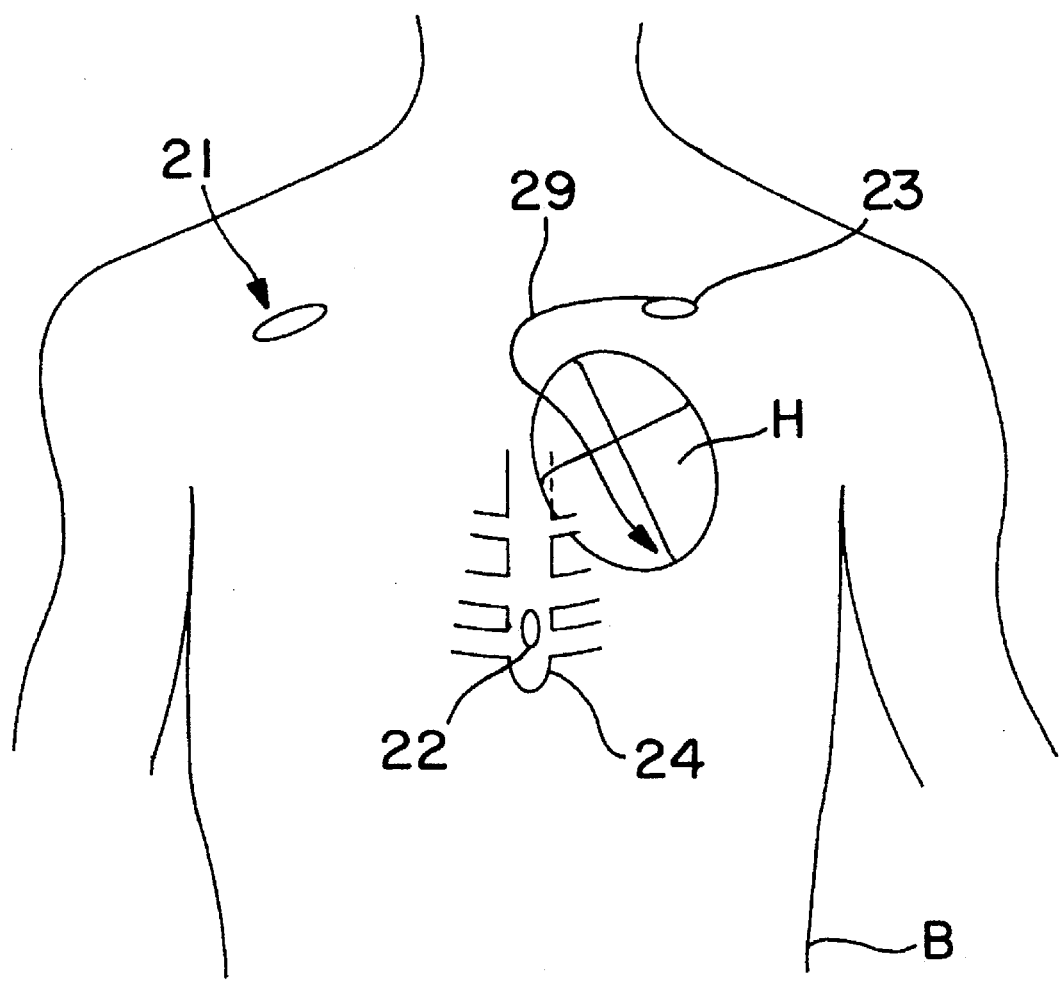
FIG. 4 is an illustration of a diagram of human body thorax having locations for implanted devices in accord with a preferred embodiment of this invention illustrated relative to the normal position of the heart.

The acoustic signal in FIG. 3 was generated by using a microphone in a stethoscope located outside the ribcage in the left pectoral region 23. Alternative and potentially preferred locations are illustrated in FIG. 4. The most preferred location has not yet been established and it will to some extent depend on the signal processing technique and other features of the rest of the system chosen by the designer and the effects of the patient's individual anatomy. In general the acoustic sensor chosen was a piezoelectric acoustic pick-up, although any type of microphone responsive to acoustic range signals will suffice. A pressure sensor, such as may be used in a pacing or sensing intracardiac lead which could be responsive in the acoustic frequency range would also be an appropriate device for sensing heart sounds. Piezoelectric sensors are preferred over piezoresistive or capacitive devices because they generate signal without power expenditure and pacemakers rely on limited battery life.

In the case of a HOCM patient, the abnormal heart sound 14 is expected as illustrated in FIG. 3. This makes signal processing relatively easy, noting that it occurs somewhere between (13) two easily detected large signals S1 and S2 but not in region 15. Other abnormal heart sounds can be similarly located with reference to the S1 and S2 sounds. This provides a window in which the aberrant sound must be found. Then its relative intensity vis-a-vis a series of such sounds across a series of heartbeats can be determined. Because the signal to noise ratio is so high for a sound like the MR sound of FIG. 3. one of ordinary skill in the signal processing art can easily construct a filter to isolate and measure the intensity of the aberrant sound. For MR measurement we prefer to look at the sound signal only in the area designated 13, and search for amplitude variations there until the aberrant sound is located. Its intensity is then determined and a value assigned, which can be stored in a memory and compared to similar sounds found in other time periods between major heart sounds like period 13. If one preferred, the aberrant sound may be located with temporal reference to features of the electrocardiogram like the QRS complex or "T" wave.

Once a reasonable expectation of high acoustic output signal is achieved, the measurement of the intensity of the signal over the noise level between the appearance of sounds $S_1$ and $S_2$ can be applied by any number of algorithms for adjusting the AV delay. Particular algorithmic processes for this kind of adjustment are described with reference to different parameters in the Sholder patents cited previously as well as in the Ishikawa article. The appropriate algorithm for the particular pacer should be selected for efficiency or cost reasons related to the design of the particular pacing system employed. Currently the preferred algorithm for responding to an MR condition is to determine if the delay is in a range approximately 60–150 ms (but within wide variants possible for some individuals) if not, move at 10 ms intervals toward the range and then compare the second to the last sound before the increment. If less intense move another 10 ms interval and so on until a minimum volume MR signal is obtained. If the AV delay starts within the acceptable range, increment toward the center of the range and keep moving, iteratively until a minimum is located. Also, if that minimum is maintained for an acceptable period the adjustment algorithm may be turned off until appropriate to restart it.

Figure 5:
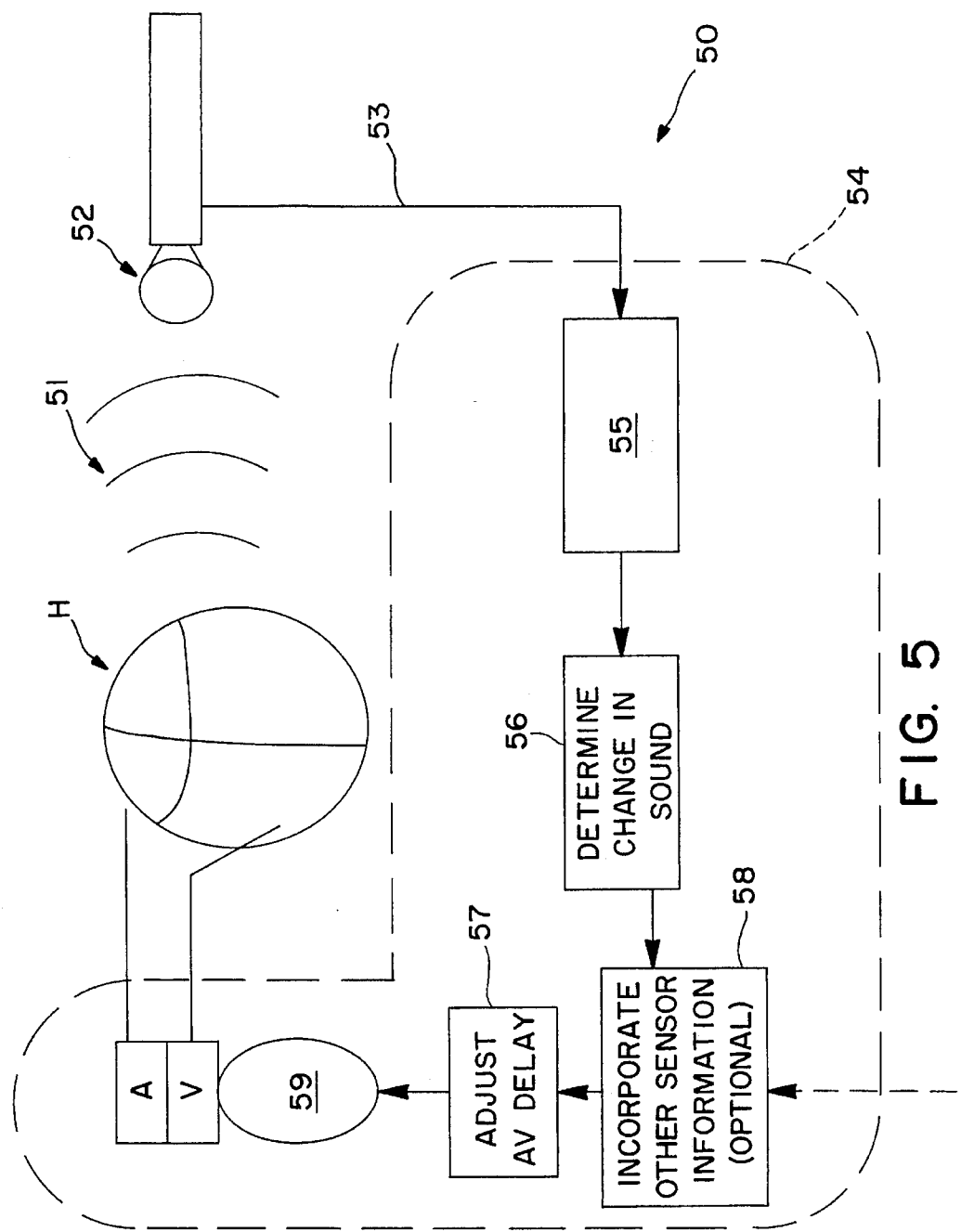
FIG. 5 is a block diagram of the flow of information from the gathering of the signals to the generation of appropriate AV delay in accord with a preferred embodiment of this invention.

Referring now to FIG. 5 in which the system for adjusting the AV delay 50 is diagrammatically detailed, the heart H can be seen generating sound output 51 which would be picked up by an acoustic detector 52 transmitted as electrical signals across a communications pathway 53 to adjustment system 54. The adjustment system 54 would require a number of processors 55, 56, 57 and 58 which may be configured in hardware or software and in various positional and temporal relationships to each other as preferred by the designer. A processor 55 must determine first whether and when during the heart beat the abnormal or MR sound is occurring. Process 55 will be initialized to search for the expected heart abnormality before beginning. A processor 56 with a memory(not shown) would determine whether and to what extent this sound has changed in intensity from the last such sound it received as input from processor 55. If other sensor information is incorporated such as activity sensors' output pressure, and so forth, (as described earlier), a processor 58 can be employed to incorporate this sensor information into the algorithm to adjust the AV delay controlled by processor 57. For instance it is known that the AV delay should be shorter during exercise all things being equal. The algorithm for finding optimal AV delay can be adjusted by monitoring patient activity to reflect this. The pacemaker circuitry 59 would then be activated according to the AV delay adjustment it receives or is instructed to perform by AV delay adjustment processor 57. It would key the delivery time of a ventricular pacing pulse against the sensed atrial depolarization or the atrial pacing pulse if one is delivered to adjust this AV interval. The exact configuration of such processors is a matter within the ordinary competence of modern pacemaker makers and therefore details of their circuits and software are not included here. Typically, however the pacemaker will have a timer or clock circuit which produces count pulses and the next ventricular pulse discharge will be timed based on a count of the timing circuit's pulsed output. The count will be lengthened or shortened by an increment chosen by the designer. In effect a timeout period will be adjusted between (either) the time an atrial depolarization is detected by an atrial sense lead (or the time of the last atrial pacing pulse) and the time the next ventricular pacing pulse is delivered. The preferred embodiment uses a sensed depolarization for the AV delay adjustment, rather than timing from the last atrial paced pulse or ventricular depolarization.

Figure 6:
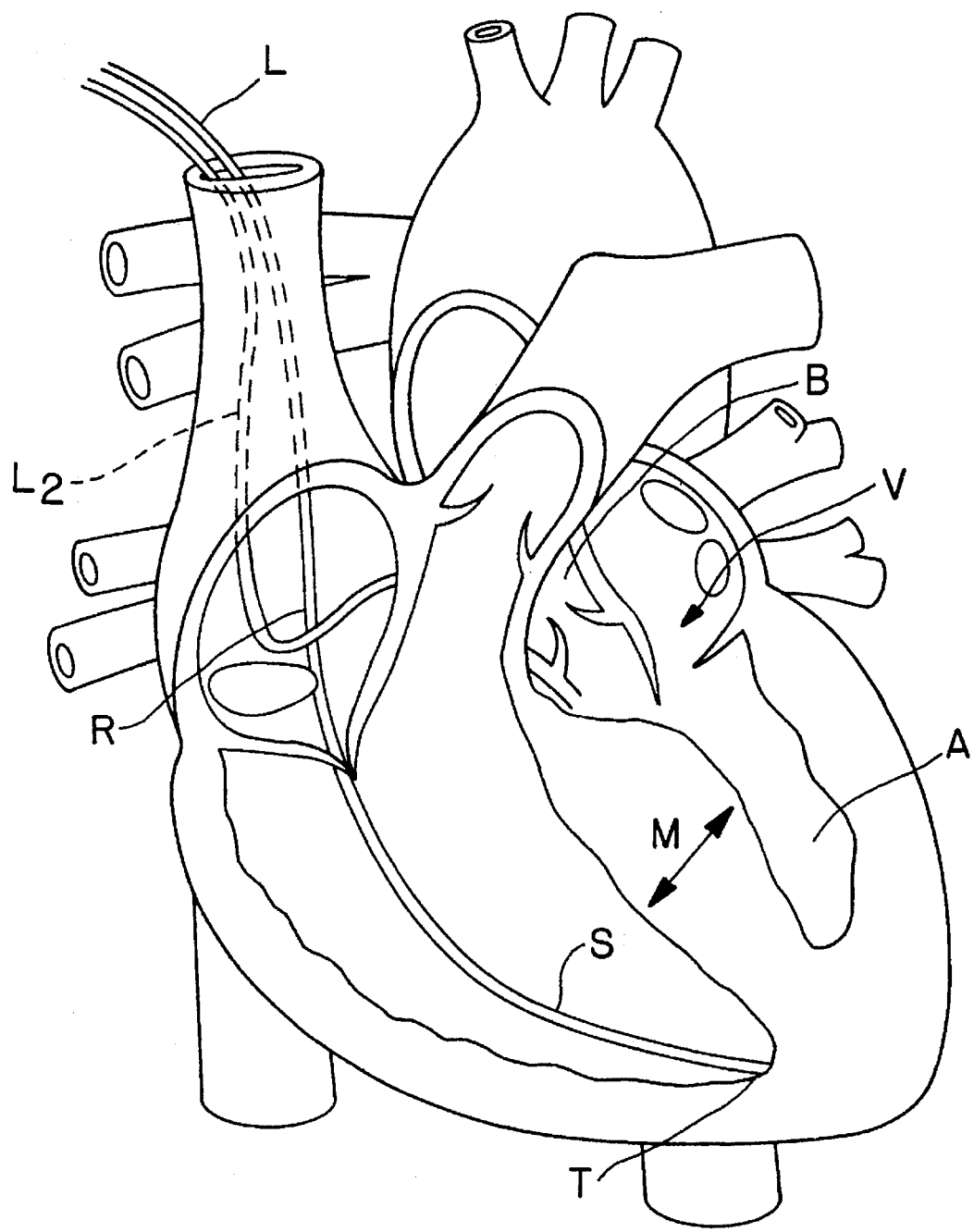

In FIG. 6 an illustration of the heart H illustrates the location of a pacing lead L with the electrodes R and T located in typical locations in the right ventricle. As can be seen in this heart, the septum muscle is grossly enlarged, creating a condition known as HOCM, i.e., one of the conditions to which this invention is directed. In this illustration, it can be seen that the expanded muscle mass of the septum M impinges upon the opening of the mitral valve V allowing for back flow or regurgitation of blood from the left ventricle back into the left atrium through the mitral valve even at the time when the left ventricle should be pumping blood out through location B into the aorta and to the body through the aortic valve. This condition illustrates the production of a sound illustrated at point 14 in line 11 of FIG. 3. Two wire pacing lead configurations (L2) have been used also and they are preferred here since a better indication of the atrial depolarization can be found with a separate atrial lead here. See "The Doctor's World," New York Times Tuesday, Mar. 2, 1993, page B6 and illustration.

The teachings of this invention may be applied to adjust the timing of pacing pulses generally where it is determined that one particular heart sound is an artifact indication of a less than optimal heart condition. In all such cases the application of a device to lower the volume of such a detected sound by adjusting the pacing delay or timing can be employed.

Accordingly, the invention here details a specific heart sound and its use to adjust pacing therapy. Those of ordinary skill in this art may apply the teachings hereof to other applications without going outside the scope of this invention which should only be taken as limited by the following claims.

We claim:

1. A method for adjusting a cardiac pacemaker by automatically responding to abnormal sounds caused by a suboptimal heart condition comprising;

isolating a particular heart sound believed to be indicative of the suboptimal heart condition at least in part by relating it temporally to the time of first ($S_1$) and second ($S_2$) heart sounds from the signal produced by an acoustic sensor adaptively situated in association with the body of a patient to receive such sounds and from them for producing high signal levels of such sounds, determining a measure of at least one characteristic of the particular heart sound, adjusting the time period before the next delivered pacing pulse until the lowest desirable measure of said at least one characteristic of said particular heart sound is detected.

2. A method as set forth in claim 1 wherein said time period adjustment is accomplished by adjusting an AV delay by incrementally changing the pacing pulse timing measured from the atrial sensed depolarization to the delivery of the ventricular pacing pulse such that the lowest desirable measure of said at least one characteristic of said particular heart sound is detected.

3. A method as set forth in claim 1 wherein said time period adjustment is accomplished by adjusting an AV delay by incrementally changing the pacing pulse timing measured from an atrial paced pulse delivery to the delivery of the ventricular pacing pulse to optimize the AV delay such that the lowest desirable measure of said at least one characteristic of said particular heart sound is detected.

4. A method as set forth in claim 1 wherein the abnormal heart condition is cardiomyopathy and the particular heart sound is MR, and wherein the time between heart sounds S1 and S2 is the temporal location for searching for said MR sound, and wherein the characteristic is from the set of sound characteristics including volume and duration.

5. A method as in claim 1 wherein said time period adjustment is accomplished by adjusting said pacing pulse timing until the desired characteristic of said particular heart sound is detected, and then leaving said adjustment to run in said pacemaker.

6. A method as set forth in claim 1 wherein said time period adjustment is accomplished automatically by a processor making timing adjustments to said pacemaker in accord with a program that seeks the desired characteristic of the heart sound.

7. A method as in claim 2 wherein said time period adjustment is accomplished by adjusting said pacing pulse timing until the lowest volume of said particular heart sound is detected, and then leaving said adjustment to run in said pacemaker in the patient.

8. A method as set forth in claim 1 wherein said time period adjustment is accomplished automatically by a processor making timing adjustments to said pacemaker in accord with a program that seeks the lowest volume acoustic feedback for the temporal location of said particular heart sound.

9. A method as set forth in claim 3 wherein a range is set previous to adjusting the AV delay to optimum such that the optimum is located within said range.

10. The method as set forth in claim 2 wherein the equation:

$$AV\ delay_{N+1} = AV\ delay_N(1 + a(MRSA_N - MRSA_{N-1}))$$

is applied by a processor to adjust the AV delay for each new heart cycle "$_{N+1}$", wherein each $_N$ indicates a heart beat cycle, $_{N-1}$ indicates a heart beat cycle previous to $_N$, $MRSA_N$ is the MR sound amplitude for heart cycle $_N$ and a is the gain for the system response.

11. The method as set forth in claim 9 wherein the equation:

$$AV\ delay_{N+1} = AV\ delay_N(1 + a(MRSA_N - MRSA_{N-1}))$$

is applied by a processor to adjust the AV delay for each new heart cycle "$_{N+1}$", wherein each $_N$ indicates a heart beat cycle, $_{N-1}$ indicates a heart beat cycle previous to $_N$, $MRSA_N$ is the MR sound amplitude for heart cycle $_N$ and a is the gain for the system response.

12. An apparatus for adjusting the timing of pacing pulses delivered by an implanted cardiac pacer based on acoustic intensity of a particular heart sound comprising:

an acoustic sensor located in association with a patient's body disposed so as to pick up heart sounds as said heart sounds occur in temporal relation to a first ($S_1$) and a second ($S_2$) heart sound in each cardiac cycle and for providing as output an intensity signal related to sensed volume of all sensed said heart sounds, a circuit for determining the intensity of one particular heart sound from the output of said acoustic sensor, a processor for adjusting the delay period between delivered pacing pulses delivered by said cardiac pacemaker adapted to make said adjustments based on the intensity of said one particular heart sound said one particular heart sound is known as Mitral Regurgitation which occurs between said first and second heart sounds.

13. An apparatus as set forth in claim 12 wherein said processor for adjusting the delay adjusts said delay so as to decrease the intensity of said one particular sound.

14. An apparatus as set forth in claim 12 wherein said processor employs the equation:

$$delay_{N+1} = delay_N(1 + a(SA_N - SA_{N-1}))$$

to adjust the pulse timing delay for each new heart cycle "$_{N+1}$", wherein each $_N$ indicates a heart beat cycle, $_{N-1}$ indicates a heart beat cycle previous to $_N$, $SA_N$ is the one particular heart sound amplitude for heart cycle $_N$ and a is the gain for the system response, such that each value determined for the variable delay $_{N+1}$ affects an AV delay value kept by a memory in the apparatus, which AV delay will be used to set the timing of the next ventricular pacing pulse to be delivered by said apparatus, timed from a last atrial event.

15. An apparatus as set forth in claim 13 wherein said processor employs the equation:

$$AV\ delay_{N+1} = AV\ delay_N(1 + a(MRSA_N - MRSA_{N-1}))$$

to adjust the AV delay for each new heart cycle "$_{N+1}$", wherein each $_N$ indicates a heart beat cycle, $_{N-1}$ indicates a heart beat cycle previous to $_N$, $MRSA_N$ is the MR sound amplitude for heart cycle $_N$ and a is the gain for the system response, such that each value determined for the variable delay $_{N+1}$ affects an AV delay value kept by a memory in the apparatus, which AV delay will be used to set the timing of the next ventricular pacing pulse to be delivered by said apparatus, timed from a last atrial event.

16. An apparatus as set forth in claim 12 wherein said processor adjusts the delay period but only within a predetermined range of time.

17. An apparatus as set forth in claim 16 wherein said processor makes adjustments to said delay period in small increments in the direction of the middle of said range and beyond it until a minimum abnormal cardiac sound is produced, then back in the opposite direction iteratively until a final minimum is found.

* * * * *